United States Patent

Dieltjens

(10) Patent No.: US 10,384,184 B2
(45) Date of Patent: Aug. 20, 2019

(54) UREA PLANT

(71) Applicant: Stamicarbon B.V., Sittard (NL)

(72) Inventor: Luc Louis Maria Dieltjens, Stein (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 15/669,818

(22) Filed: Aug. 4, 2017

(65) Prior Publication Data

US 2017/0326521 A1    Nov. 16, 2017

Related U.S. Application Data

(63) Continuation of application No. 13/805,633, filed as application No. PCT/NL2011/050458 on Jun. 24, 2011, now abandoned.

(30) Foreign Application Priority Data

Jun. 24, 2010 (EP) .................................. 10167180
Jul. 1, 2010 (EP) .................................. 10168065

(51) Int. Cl.
*B01J 12/00* (2006.01)
*C07C 273/04* (2006.01)

(52) U.S. Cl.
CPC ............. *B01J 12/005* (2013.01); *B01J 12/00* (2013.01); *C07C 273/04* (2013.01); *Y02P 20/142* (2015.11)

(58) Field of Classification Search
CPC ... C07C 273/00; C07C 273/02; C07C 273/04; Y02P 20/00; Y02P 20/10; Y02P 20/14–142; B01J 12/00; B01J 12/005
See application file for complete search history.

(56) References Cited

U.S. PATENT DOCUMENTS

| 3,258,486 | A | * | 6/1966 | Cook .................... C07C 273/04 202/158 |
| --- | --- | --- | --- | --- |
| 3,691,729 | A | | 9/1972 | De Rooy et al. |
| 4,218,397 | A | * | 8/1980 | Konoki .................. C07C 273/04 423/359 |
| 4,864,059 | A | | 9/1989 | Fujii |
| 5,096,599 | A | | 3/1992 | Granelli |
| 5,523,483 | A | | 6/1996 | Singh et al. |
| 5,582,656 | A | | 12/1996 | Kangas et al. |
| 6,723,876 | B2 | | 4/2004 | Speth |
| 2010/0016635 | A1 | | 1/2010 | Singh |

FOREIGN PATENT DOCUMENTS

| CN | 85 1 07834 | 6/1986 |
| --- | --- | --- |
| CN | 1554643 | 12/2004 |
| CN | 1923344 | 3/2007 |
| JP | 52-43800 | 11/1977 |

(Continued)

OTHER PUBLICATIONS

International Search Report for PCT/NL2011/050458, dated Sep. 30, 2011, 2 pages.

(Continued)

*Primary Examiner* — Natasha E Young
(74) *Attorney, Agent, or Firm* — Morrison & Foerster LLP

(57) ABSTRACT

The invention relates to a urea plant with a $CO_2$ and a $NH_3$ feed, which comprises a purge line, characterized in that the purge line is connected with a fuel gas input line of a utility plant or an $NH_3$ plant.

18 Claims, 1 Drawing Sheet

(56) References Cited

FOREIGN PATENT DOCUMENTS

| | | |
|---|---|---|
| JP | 8-511829 | 12/1996 |
| JP | 9-3032 | 1/1997 |
| JP | 2000-159519 | 6/2000 |
| JP | 2002-114752 | 4/2002 |
| JP | 2003-526512 | 9/2003 |
| WO | WO-95/00674 | 1/1995 |

OTHER PUBLICATIONS

Notice of Reasons for Rejection for JP 2013-516517, dated Feb. 9, 2015, 4 pages.
Office Action in Eurasian Patent Application No. 201390024/31, dated Jul. 11, 2014, 1 page. (English language translation).

\* cited by examiner

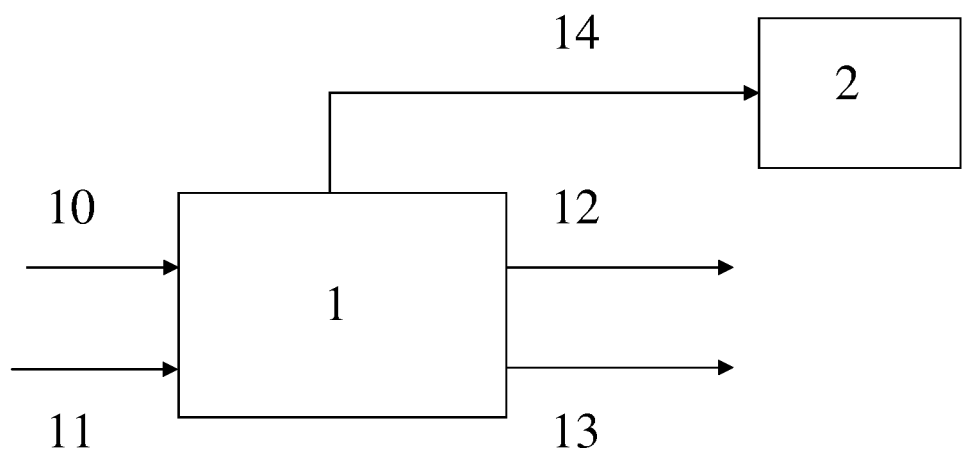

UREA PLANT

CROSS-REFERENCE TO RELATED APPLICATIONS

This Application is a Continuation of application Ser. No. 13/805,633, having an international filing date of 24 Jun. 2011, which is the national phase of PCT application PCT/NL2011/050458, published as WO/2011/162610, having an international filing date of 24 Jun. 2011, which claims benefit of European patent application Nos. 10167180.8 filed 24 Jun. 2010, and 10168065.0 filed 1 Jul. 2010. The contents of the above patent applications are incorporated by reference herein in their entirety.

BACKGROUND OF THE INVENTION

In commercial urea processes, urea ($NH_2CONH_2$) is produced by reacting ammonia ($NH_3$) and carbon dioxide ($CO_2$) at elevated temperature and pressure according to the reactions:

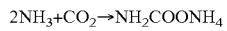

$$2NH_3 + CO_2 \rightarrow NH_2COONH_4$$

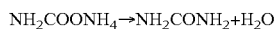

$$NH_2COONH_4 \rightarrow NH_2CONH_2 + H_2O$$

An overview of commercial processes using this chemistry is given e.g. in Ullmann Encyclopedia, 2005 Wiley-VCH verlag, Weinheim, Germany, chapter Urea. All processes use $NH_3$ and $CO_2$ as feedstock. These feedstocks, usually both originating from a ammonia plant contain impurities. The impurities do not react in the abovementioned chemistry, and therefore need to be purged from the urea plant in order to prevent their accumulation.

The invention relates to a urea plant comprising synthesis equipment, synthesis piping, a $CO_2$ and a $NH_3$ feed, and a purge stream. In this purge stream, part of, or all inert gases that are present in the $CO_2$ and $NH_3$ feed, as well as part, or all, of any other inert gases fed to the urea plant are released from the urea plant. Inert gases, in this context are defined as any gaseous components that do not contribute to the chemical production of urea.

Both feedstocks are usually originating from an ammonia plant. Although an ammonia plant is a net heat producer and a urea plant is a net heat (steam) consumer, and it is normal practice to integrate the steam systems of both plants, net heat is required, which is generally obtained from burning fuel.

In order to reduce the production of greenhouse gases caused by burning fuel, it is a purpose of the invention to reduce the fuel consumption required for the production of urea.

This purpose is obtained by connecting the purge line with a fuel gas feed of a utility plant or an ammonia plant, the fuel consumption can be reduced by 2%, which for an average urea/ammonia complex corresponds with a saving of about $7 \times 10^6$ kg natural gas/year.

The $NH_3$ feed typically comprises also minor amounts of $CH_4$.

Methane ($CH_4$) contributes to the growing global background concentration of tropospheric ozone ($O_3$), an air pollutant associated with premature mortality. Methane and ozone are also important greenhouse gases.

A further advantage of the invention is that methane emissions of the urea plant are reduced, which decreases surface ozone and slowing global climate warming.

The $CO_2$ feed is generally provided with an additional oxygen stream, generally originating from air. The oxygen serves as an agent to prevent excessive corrosion of the synthesis equipment and the synthesis piping. As the oxygen does not contribute to the production of urea, it is vented with the purge gas. Excessive corrosion is prevented when the oxygen concentration in the purge gas is in the range of 5-20 mol %

As the $NH_3$ feed and the $CO_2$ feed comprise minor amounts of $H_2$, the purge stream is very likely to be inflammable even before the addition of an oxidizing agent (e.g. air). Because of this inflammable character of the purge gas stream, it is unsafe to transport this gas (e.g. via pipelines) over some distance. In contrast, it is common practice up to now to vent this purge gas via shortest possible connections into the atmosphere.

By the use of a duplex ferritic-austenitic steel with a high content of Cr and N and a low content of Ni, as described in WO9500674, as a material of construction for the synthesis equipment and synthesis piping, oxygen needs no longer be supplied to the synthesis to prevent corrosion, or only in very low concentrations in the carbon dioxide feed e.g. <0.05 vol % of oxygen. Said duplex ferritic-austenitic steel is preferably a duplex, stainless steel alloy that contains, in % by weight: 0-0.05 C; 0-0.8 Si; 0.3-4 Mn; 28-35 Cr; 3-10 Ni; 1.0-4.0 Mo; 0.2-0.6 N; 0-1.0 Cu; 0-2.0 W; 0-0.010 S; 0-0.2 Ce, the remainder being Fe and normally occurring impurities and additives, the ferrite content being 30-70% by volume.

The use of said duplex ferritic-austenitic steel allows a reduction of the additional oxygen stream in the $CO_2$ feed such that the oxygen concentration in the purge gas can be reduced to between 0-10 mol % or 0-1 mol %, without the risk of excessive corrosion taking place. Preferably oxygen is essentially absent in the purge gas. It is surprising that the purge gas stream, essentially without oxygen, now can be transported (e.g. by pipelines) without associated safety risks, to be used as a fuel gas.

The purge line of the urea plant of the invention is connected with a fuel gas input line of a utility plant or an $NH_3$ plant. Preferably the purge stream is directed to the reformer section in an ammonia plant, or to the fuel gas supply of a steam boiler.

The invention will be elucidated hereinafter on the basis of FIG. 1, without being restricted to this embodiment.

FIG. 1 shows a urea plant (1) comprising a $CO_2$ feed (10) and a $NH_3$ feed (11). Solid urea leaves the plant via line 12. Water is purged via line 13. Purge line (14) is connected with a fuel gas input line of a utility plant or an $NH_3$ plant (2).

The invention claimed is:

1. A method to reduce fuel consumption of a utility plant, which method comprises feeding a purge gas stream from a urea production plant, said urea production plant comprising a $CO_2$ feed and an $NH_3$ feed, into a fuel gas input line of said utility plant;
   wherein said purge gas stream comprises at least one impurity from said $CO_2$ feed and at least one impurity from the $NH_3$ feed, and wherein the utility plant comprises a steam boiler and the purge stream is fed into a fuel gas supply of a steam boiler in said utility plant.

2. The method of claim 1, wherein the purge gas stream contains oxygen at a concentration in the range of 0-10 mol %.

3. The method of claim 2, wherein the purge gas contains oxygen at a concentration in the range of 0-1 mol %.

4. The method of claim 3 wherein oxygen is essentially absent in the purge gas stream.

5. The method of claim 1, wherein the urea production plant comprises synthesis equipment and synthesis piping and the material used for the synthesis equipment and synthesis piping a duplex ferritic-austenitic that contains, in % by weight:

0-0.05 C;
0-0.8 Si;
0.3-4 Mn;
28-35 Cr;
3-10 Ni;
1.0-4.0 Mo;
0.2-0.6 N;
0-1.0 Cu;
0-2.0 W;
0-0.010 S;
0-0.2 Ce,
the remainder being Fe and normally occurring impurities and additives, having a ferrite content 30-70% by volume.

6. The method of claim 1 wherein said purge gas stream is derived solely from said urea production.

7. A urea production process, wherein urea is produced by reacting ammonia ($NH_3$) and carbon dioxide ($CO_2$), carried out in a urea plant comprising a $CO_2$ and a $NH_3$ feed, wherein the plant further comprises a purge line for a purge gas stream, wherein said purge gas stream comprises at least one impurity from said $CO_2$ feed and at least one impurity from said $NH_3$ feed, wherein the purge line is connected with a fuel gas input line of a utility plant, and wherein the method comprises using the purge gas as a fuel gas in said utility plant, wherein said utility plant comprises a steam boiler, and wherein the purge stream is directed to the fuel gas supply of said steam boiler.

8. A urea production process according to claim 7, wherein the oxygen concentration in the purge gas is in the range of 0-10 mol %.

9. A urea production process according to claim 7, wherein the oxygen concentration in the purge gas is in the range 0-1 mol %.

10. A urea production process according to claim 7, wherein oxygen is essentially absent in the purge gas.

11. A urea production process according to claim 7, wherein the plant comprises synthesis equipment and synthesis piping wherein as material for the synthesis equipment and synthesis piping a duplex ferritic-austenitic is used that contains, in % by weight: 0-0.05 C; 0-0.8 Si; 0.3-4 Mn; 28-35 Cr; 3-10 Ni; 1.0-4.0 Mo; 0.2-0.6 N; 0-1.0 Cu; 0-2.0 W; 0-0.010 S; 0-0.2 Ce, the remainder being Fe and normally occurring impurities and additives, the ferrite content being 30-70% by volume.

12. A process according to claim 7, wherein said purge line is configured to conduct purge gas derived only from said urea production.

13. A method to reduce fuel consumption of an ammonia plant or a utility plant, which method comprises feeding a purge gas stream from a urea production plant, said urea production plant comprising a $CO_2$ feed and an $NH_3$ feed, into a fuel gas input line of said ammonia plant or utility plant;
wherein said purge gas stream comprises at least one impurity from said $CO_2$ feed and at least one impurity from the $NH_3$ feed wherein the $CO_2$ feed comprises $H_2$ and less than 0.05 vol % of oxygen.

14. The method of claim 13, wherein the purge stream is fed into a reformer section in said ammonia plant.

15. The method of claim 13, wherein the $NH_3$ feed comprises $H_2$.

16. A urea production process, wherein urea is produced by reacting ammonia ($NH_3$) and carbon dioxide ($CO_2$), carried out in a urea plant comprising a $CO_2$ and a $NH_3$ feed, wherein the plant further comprises a purge line for a purge gas stream, wherein said purge gas stream comprises at least one impurity from said $CO_2$ feed and at least one impurity from said $NH_3$ feed, wherein the purge line is connected with a fuel gas input line of a utility plant or an $NH_3$ plant, and wherein the method comprises using the purge gas as a fuel gas in said utility plant or $NH_3$ plant, wherein the $CO_2$ feed comprises $H_2$ and less than 0.05 vol % of oxygen.

17. A urea production process according to claim 16, wherein the $NH_3$ feed comprises $H_2$.

18. A urea production process according to claim 16 wherein the purge stream is directed to the reformer section of said $NH_3$ plant.

* * * * *